(12) United States Patent
Kim et al.

(10) Patent No.: US 8,845,445 B2
(45) Date of Patent: Sep. 30, 2014

(54) FEEDBACK APPARATUS AND METHOD FOR IMPROVING COCKING LOOSENING

(75) Inventors: Jin Wook Kim, Seoul (KR); An Jin Park, Seoul (KR); Hyeong Rae Choi, Seoul (KR); Sung Kuk Chun, Asan-si (KR); Dong Hoon Kang, Yangsan-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/604,803

(22) Filed: Sep. 6, 2012

(65) Prior Publication Data

US 2014/0066219 A1    Mar. 6, 2014

(51) Int. Cl.
  *A63B 57/00*    (2006.01)
  *A63F 7/20*    (2006.01)

(52) U.S. Cl.
  USPC .......................... 473/212; 473/219; 273/317.2

(58) Field of Classification Search
  USPC ................. 473/131, 207, 212, 219–222, 409; 463/3; 273/317.2
  See application file for complete search history.

(56) References Cited

U.S. PATENT DOCUMENTS

| | | | |
|---|---|---|---|
| 4,023,812 A * | 5/1977 | Lorang | 473/227 |
| 5,108,103 A * | 4/1992 | Rilling | 473/213 |
| 5,743,805 A * | 4/1998 | Richter | 473/213 |
| 5,772,522 A * | 6/1998 | Nesbit et al. | 473/222 |
| 6,567,536 B2 | 5/2003 | McNitt et al. | |
| 7,033,281 B2 * | 4/2006 | Carnahan et al. | 473/221 |
| 7,871,333 B1 * | 1/2011 | Davenport et al. | 473/223 |
| 8,109,816 B1 * | 2/2012 | Grober | 463/3 |
| 8,425,340 B2 * | 4/2013 | Davenport | 473/223 |
| 2003/0040380 A1 * | 2/2003 | Wright et al. | 473/409 |
| 2005/0215336 A1 * | 9/2005 | Ueda et al. | 473/131 |
| 2005/0272517 A1 * | 12/2005 | Funk et al. | 473/222 |
| 2006/0084516 A1 * | 4/2006 | Eyestone et al. | 473/219 |
| 2006/0287118 A1 * | 12/2006 | Wright et al. | 473/131 |
| 2010/0210371 A1 * | 8/2010 | Sato et al. | 473/223 |
| 2012/0108351 A1 * | 5/2012 | Tamura | 473/213 |

FOREIGN PATENT DOCUMENTS

| | | |
|---|---|---|
| KR | 10-2000-0063845 | 11/2000 |
| KR | 10-2001-0047628 | 6/2001 |
| KR | 10-0772497 B1 | 10/2007 |
| KR | 10-2009-0105031 | 10/2009 |
| KR | 10-2011-0101628 A | 9/2011 |
| KR | 10-2011-0122656 | 11/2011 |
| KR | 10-2012-0021848 A | 3/2012 |
| WO | WO 2006/081395 A2 | 8/2006 |
| WO | WO 2009/060010 A2 | 5/2009 |

* cited by examiner

*Primary Examiner* — Milap Shah
(74) *Attorney, Agent, or Firm* — NSIP Law

(57) ABSTRACT

A cocking loosening feedback method includes sensing sequential three-dimensional direction information of a golf club and three-dimensional direction information of the arm a user, analyzing the change of an angle between both three-dimensional information with respect to time, generating a cocking loosening evaluation variable based on the difference between the cocking loosening point and the impact point and the difference between the backswing top point and the impact point in the analyzed three-dimensional information, analyzing the evaluation variable based on a predetermined criterion to evaluate the cocking loosening, and providing its feedback information to the user.

14 Claims, 7 Drawing Sheets

Fig.6

| k | FEEDBACK | SCORE |
|---|---|---|
| 0.45~0.55 | IDEAL COCKING LOOSENING | 100 |
| 0.55~0.65 | SLIGHTLY FAST COCKING LOOSENING | 80 |
| 0.65~0.75 | FAST COCKING LOOSENING | 60 |
| 0.75~1.00 | VERY FAST COCKING LOOSENING | 40 |
| 0.35~0.45 | SLOW COCKING LOOSENING | 80 |

FEEDBACK APPARATUS AND METHOD FOR IMPROVING COCKING LOOSENING

BACKGROUND

1. Field

The present disclosure relates to cocking loosening evaluation of an angle of the wrist during a golf swing, and more particularly, to apparatus and method for evaluating a cocking loosening point at a swinging motion of a user and providing a graded feedback.

2. Description of the Related Art

Even though the golf has become popular and related industries have been developed, the golf is one of sports whose skills are not easily trained. This is because the golf swing requires a complicated mechanism composed of fixation of the line of vision, center of gravity, movement, swing trajectory or the like, rather than physical conditions. In order to overcome this, there is needed a device which may induce improvement of swing by feeding through automatic analysis and rating of essential swing elements and their visualized information for correct swing to a user.

In such an automatic analyzing device for essential elements of golf swing, there is an increasing demand and importance of cocking which is a key element for the improvement of a flying distance and a slice. The cocking represents the change of an angle between the arm and a golf club, namely an angle of the wrist, during the golf swing which is performed sequentially with essential behaviors in the order of addressing, backswing, backswing top, downswing, impact, and follow-through. In a desirable cocking loosening, substantially a right-angle cocking is made in the backswing top, and in the downswing, while keeping the cocking of the backswing top, the cocking loosening is made at the point close to an impact. The desirable cocking is very important for the improvement of swing postures since it has a very close relation with accurate impact, prevention of a slice, and the increase of a flying distance caused by the improvement of a club head speed.

In a conventional technique related to the improvement of cocking, the movement of a golf club and the arm of the user is restricted or reformed by using a separate golf swing exercise instrument, or the muscular strength for swing of the body such as the wrist is simply reinforced for effective improvement of a flying distance, which can be expected by correct cocking, rather than improving the cocking.

However, in the method where the movement is restricted or reformed, a specially designed club or instrument should be used for the cocking training. In addition, in the training for reinforcing the muscular strength to improve a flying distance, the training is focused simply on the increase of the muscular power of the wrist or arm, which is insufficient for exercising cocking loosening or correct wrist movement. Therefore, such conventional techniques may give a bad influence in solving problems such as inaccurate impact and slice.

SUMMARY

The present disclosure is directed to providing a method which allows a user to recognize a cocking loosening point in his swinging motion and solve problems of the swinging motion by himself, rather than simply reinforcing the muscular strength, without using a separately designed device or club which restricts or reforms the movement of the user.

In one aspect, there is provided a cocking loosening feedback apparatus, which includes: a sensing unit for sensing three-dimensional direction information of a golf club and three-dimensional direction information of the arm in a golf swinging motion of a user; an analyzing unit for analyzing an angle between both three-dimensional direction information with respect to time to extract a backswing top point, a cocking loosening point and an impact point; an evaluation variable generating unit for generating a cocking loosening evaluation variable of the user based on the difference between the cocking loosening point and the impact point and the difference between the backswing top point and the impact point; and an output unit for providing feedback information to the user based on the cocking loosening evaluation variable.

In another aspect, there is provided a cocking loosening feedback method, which includes: sensing three-dimensional direction information of a golf club and three-dimensional direction information of the arm in a golf swinging motion of a user; analyzing an angle between both three-dimensional direction information with respect to time to extract a backswing top point, a cocking loosening point and an impact point; generating a cocking loosening evaluation variable of the user based on the difference between the cocking loosening point and the impact point and the difference between the backswing top point and the impact point; and providing feedback information to the user based on the cocking loosening evaluation variable.

According to an aspect of the present disclosure, when a user makes a golf swing, it is possible to analyze and evaluate an angle between the arm and a golf club, and then provide a feedback comment and a score to the user for the improvement of cocking.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 6 is a table exemplarily showing a feedback and a score according to a K value (evaluation variable) according to an embodiment of the present disclosure;

DETAILED DESCRIPTION

Hereinafter, embodiments of the present disclosure will be described in detail with reference to the accompanying drawings.

Figure 1:
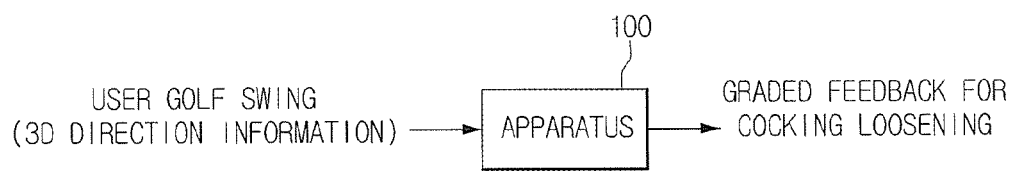
FIG. 1 is a schematic block diagram showing a device for outputting cocking loosening evaluation according to an embodiment of the present disclosure.

Referring to FIG. 1, an apparatus 100 for receiving a golf swing motion of a user and providing graded feedback about cocking loosening according to an embodiment of the present disclosure is shown.

The cocking loosening feedback apparatus 100 according to an embodiment of the present disclosure senses a cocking loosening phenomenon based on an angle between a golf club and the arm (three-dimensional direction information) in a sequential golf swinging motion of the user, evaluates a cocking loosening point, and provides graded feedback to the user for the improvement of cocking loosening for the golf swing of the user.

Figure 2:
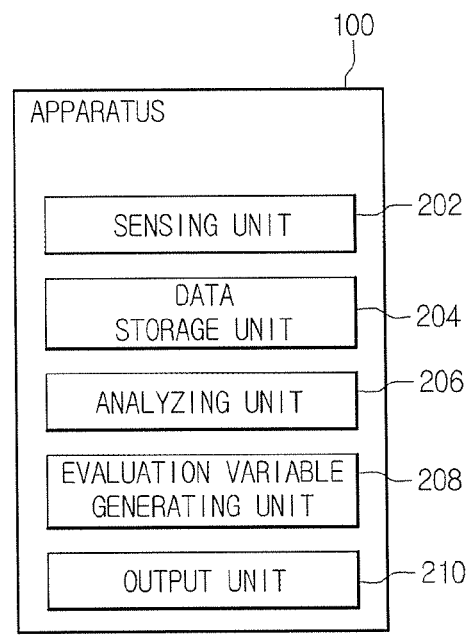
FIG. 2 is a diagram showing a cocking loosening feedback apparatus according to an embodiment of the present disclosure.

Referring to FIG. 2, the cocking loosening feedback apparatus 100 according to an embodiment of the present disclosure includes a sensing unit 202 for sensing three-dimensional information of the golf club and three-dimensional direction information of the arm of the user, which is sequential in the golf swing, a data storage unit 204 for collecting, synchronizing and storing the sensed three-dimensional direction information, an analyzing unit 206 for analyzing an angle between both three-dimensional direction information with respect to time to extract a backswing top point, a cocking loosening point and an impact point based on the stored data information, an evaluation variable generating unit 208 for generating a cocking loosening evaluation variable of the user based on the difference between the cocking loosening point and the impact point and the difference between the backswing top point and the impact point, and an output unit 210 for providing feedback information to the user based on the cocking loosening evaluation variable.

In the apparatus according to the embodiment of the present disclosure, the sensing unit 202 receives a golf swinging motion (three-dimensional direction information) of the user and sends a direction vector or coordinate system (hereinafter, referred to as direction information) of a golf club and the arm with respect to the three-dimensional space to the data storage unit 204 in order to measure a cocking angle between the golf club and the arm of the user.

In the cocking loosening feedback apparatus 100 according to an embodiment of the present disclosure, the sensing unit 202 may collect data about a swing posture through sensors in order to measure the cocking, namely the change of an angle between the arm and the golf club during the golf swing of the user. In order to measure the direction information in the three-dimensional space for the measurement of the cocking angle, various sensors may be used. For example, a vision sensor or an IMU sensor may be used, or both the vision sensor and the IMU sensor may be used together in hybrid manner. In the case where both the vision sensor and the IMU sensor are used, the coordinate system may be unified by means of calibration, the direction information of the golf club may be measured through the vision sensor, the direction information may be measured by attaching the IMU sensor to the arm, and the direction information of the arm may be measured by the vision sensor. The vision sensor may employ various kinds of sensors such as a Charged Coupled Device (CCD), a Pinned Photo Diode (PPD), a Charge and Injection Device (CID), an Active Pixel Sensor (APS), an Active Column Sensor (ACS) or the like.

In the sensing unit 202 employed in the apparatus according to an embodiment of the present disclosure, the sensor used for sensing the golf swinging motion may adopt a contact type or a non-contact type. In detail, in the contact type, in a state where the sensor is attached or touches the body of the user, the location, rotation or movement information of the touched sensor is received to track the motion. Representatively, an optical motion tracker (where a marker is attached to a body to be traced and a motion of a marker in a three-dimensional space according to the motion of the body is traced), an acceleration sensor (which is attached to the body of the user to output an acceleration value of the attachment portion and estimate the motion), a pressure sensor (which measures an input pressure, for example, and in a case where pressure sensors are installed at bottoms of both feet, the pressure sensor may measure the change of a reaction of the ground according to time), an IMU sensor (which outputs the degree of turns of the portion of the body where the sensor is attached) or the like may be used. In the non-contact type, a physical motion is traced using a camera (or, a vision sensor) without attaching or touching a sensor or other substances to the body, and a user may make natural swing since the user does not feel foreign.

According to an embodiment of the present disclosure, the data storage unit 204 continuously receives three-dimensional direction information of the arm and the golf club, respectively, during golf swing of the user input by the sensing unit, collects the information till the end of swing, and transmits the information to the analyzing unit 206. The end point of swing which is an end point of data collection may be defined in various ways, for example a point where the three-dimensional direction information collected or input by the user does not change for a predetermined period. In addition, since the collected three-dimensional direction information of the arm and the golf club is accurately synchronized on the time axis and obtained, the direction information of the arm and the direction information of the golf club obtained at a certain time point may be stored in pairs.

Figure 3:
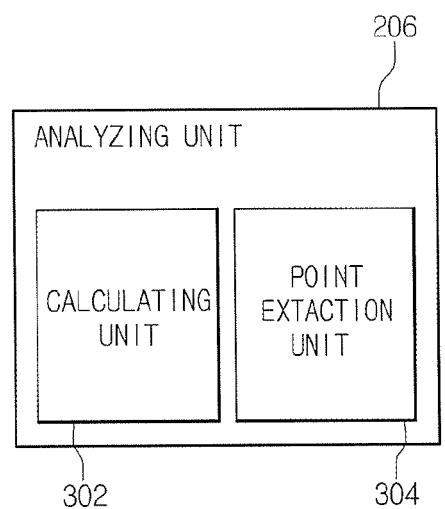
FIG. 3 is a diagram showing an analyzing unit of the cocking loosening feedback apparatus according to an embodiment of the present disclosure.

Referring to FIG. 3, the configuration of the analyzing unit 206 employed in the cocking loosening feedback apparatus according to an embodiment of the present disclosure is shown. The sequential three-dimensional direction information of the arm and the golf club is input to the analyzing unit 206, and the analyzing unit may output an analysis result of the three-dimensional direction information. The analysis result may include a calculation value of the wrist cocking angle, an important swing point or the like. The analyzing unit 206 may include a calculating unit 302 and a point extracting unit 304.

The calculating unit 302 according to an embodiment of the present disclosure may calculate the change of a cocking angle (of the wrist) based on the three-dimensional direction information stored in the data storage unit 204 and the relative angle change of the golf club based on the location of the golf club at the address posture. The cocking angle may be defined as an angle between the arm and the golf club, and the address posture may be defined as a direction where the club head is oriented perpendicularly to the ground. Therefore, the cocking angle may be obtained by calculating the angle of the direction information of the arm and the golf club in the three-dimensional space obtained from the sensing unit 202 of the cocking loosening feedback apparatus according to an embodiment of the present disclosure and input and synchronized by the data storage unit 204. For example, in case where a three-dimensional direction vector ($x_{arm}$) of the arm and a direction vector ($x_{club}$) of the golf club are obtained, a cocking angle ($\theta$) may be calculated according to Equation 1 below.

$$x_{arm} \cdot x_{club} = \|x_{arm}\| \|x_{club}\| \cos(\theta), \ 0 \leq \theta \leq \pi \qquad \text{<Equation 1>}$$

Figure 4:
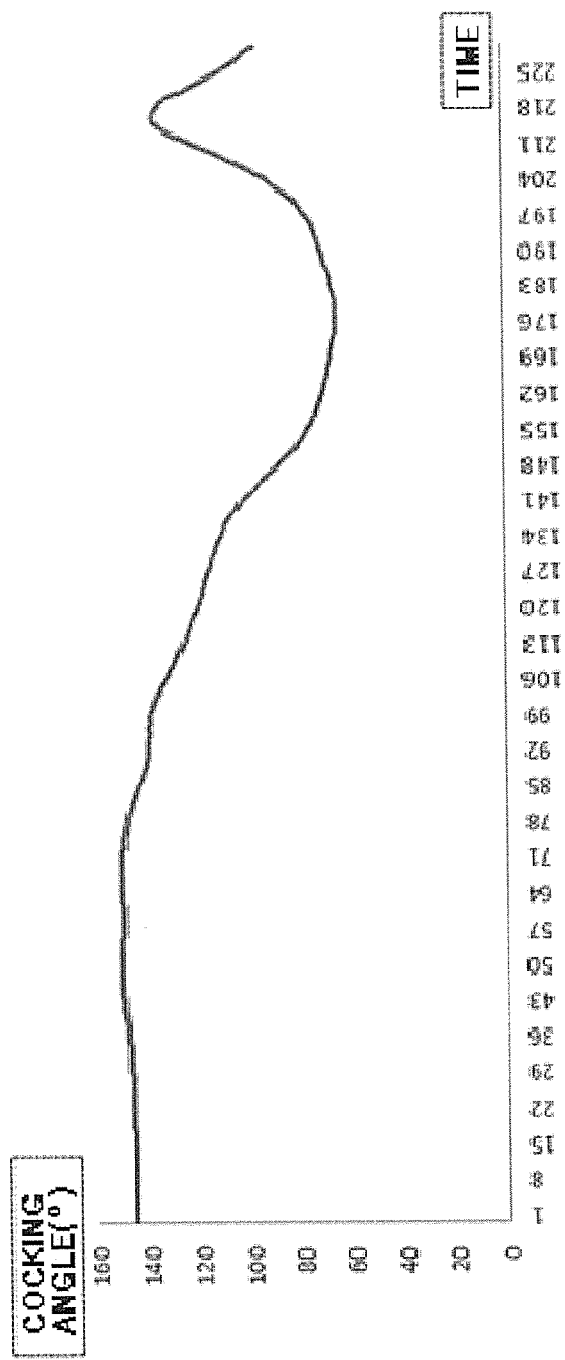
FIG. 4 is a graph showing the change of a cocking angle according to time according to an embodiment of the present disclosure.

The graph shown in FIG. 4 expresses the cocking angles for all direction vector pairs (three-dimensional direction information) of the arm and the golf club, synchronized in the data group obtained from the data storage unit 204, which are calculated by the above method, on the time axis.

In the cocking loosening feedback apparatus according to an embodiment of the present disclosure, the point extracting unit 304 may extract an important swing point according to a relative turning angle of the golf club based on the address point. The important swing point may include a backswing top point, an impact point, and a cocking loosening point for evaluating the cocking loosening.

The cocking loosening point of a desirable golf swing demands that downswing may be performed while keeping the cocking angle of the wrist after the backswing top posture of the golf swing and the cocking loosening may be generated at a point as closest to the impact point when the ball is impacted as possible. Therefore, the important posture (point) of the golf swing required for evaluating the cocking loosening may be a backswing top point, an impact point or the like.

Figure 5:
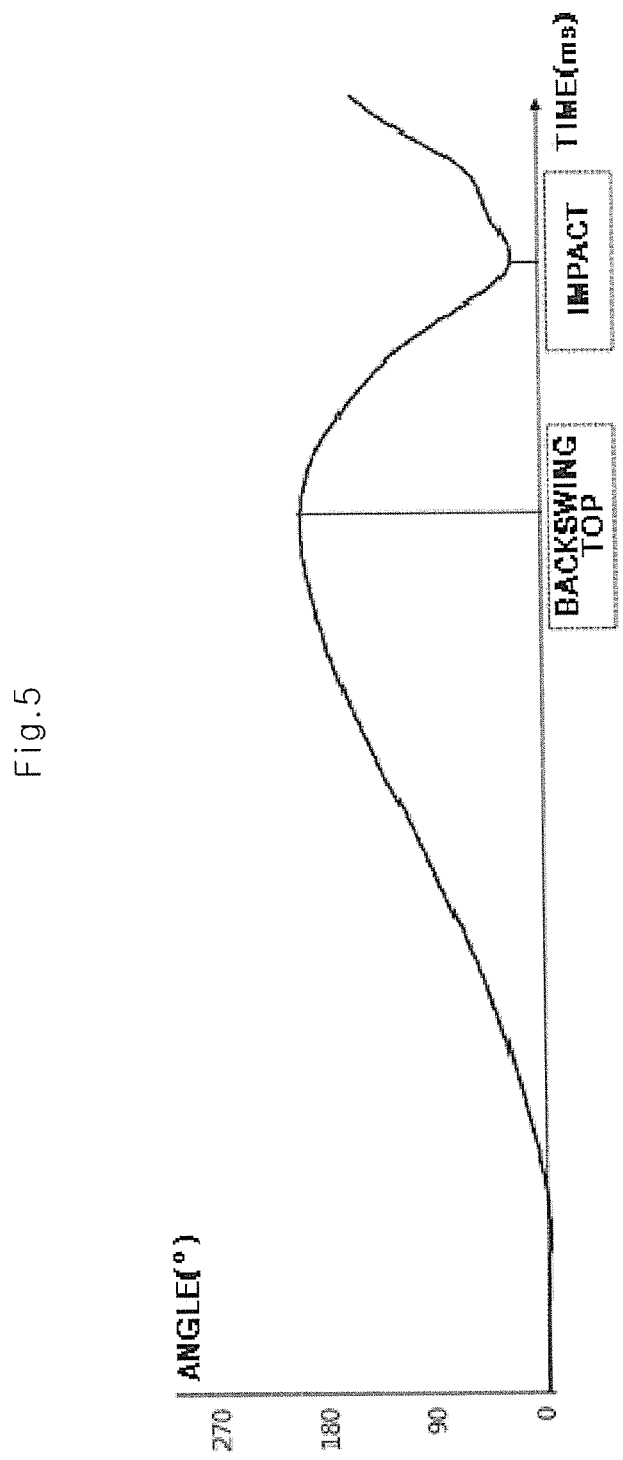
FIG. 5 is a graph showing the change of a turning angle of a golf club and important swing points based on the angle, when a swing is made according to time according to an embodiment of the present disclosure.
Figure 7:
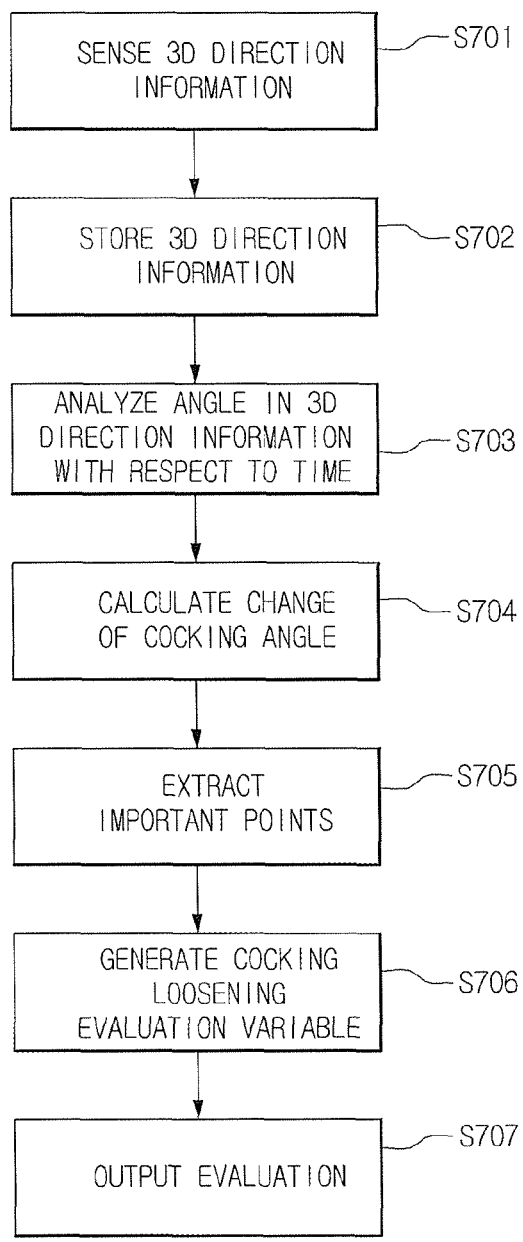
FIG. 7 is a flowchart for illustrating a cocking loosening feedback method according to an embodiment of the present disclosure.

Referring to FIG. 5, the graph of the relative turning angle of the golf club in the progress of swing is shown based on the golf club at the address point. In view of the relative turning angle of the golf club expressed by the time axis, the golf club turning angle will have a maximum value at the backswing top point and will not change greatly for a certain period, and so the angular speed will be close to 0. In addition, in case of the moment of impact, the turning angle of the golf club will decrease before and after the moment of impact and then increases, and the angular speed will change from a negative value to a positive value. Therefore, the zero-crossing point of the angular speed may be defined as the impact point. In other case, the backswing top point may be defined as the turning angle of the golf club, and the moment of impact may be defined as the moment when the ball starts moving when being actually hit, which may be sensed by a sensor.

In order to determine important postures (points) according to an embodiment of the present disclosure, a marker or marker-less motion recognition method using a vision sensor or an IMU sensor may be used. In addition, a heuristic method using a cocking angle expressed on the time axis, which may be obtained in the cocking angle calculating process, may also be used.

Figure 8:
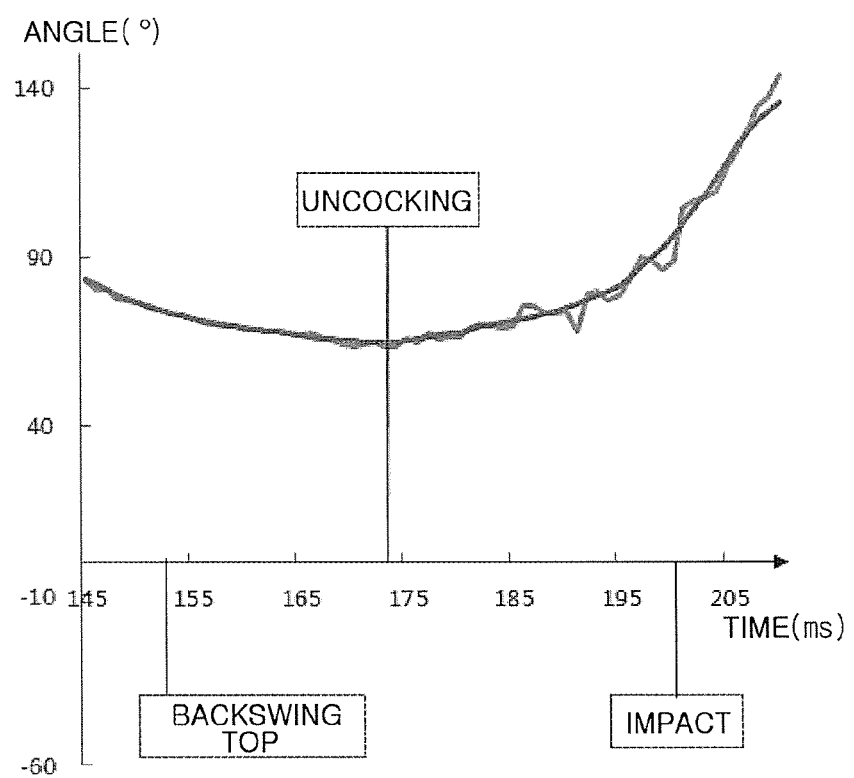
FIG. 8 is a graph showing a cocking loosening point according to an embodiment of the present disclosure.

In this specification, the point when the cocking loosening (uncocking) is generated may mean a point when the angle of the wrist which is an angle between the arm and the club loosens during the swing from the backswing top to the impact, namely in the downswing region. Referring to FIG. 8, the gray color represents an angle of the wrist calculated by two Inertial Measurement Units (IMUS) provided at the golf club and the arm, and the black color represents the data smoothed (to remove noise). In addition, the cocking loosening point may be defined as a point where the wrist has a minimal angle in the downswing region.

According to an embodiment of the present disclosure, the cocking loosening feedback apparatus may extract the closeness of the cocking loosening point existing between the backswing top and the impact point to the impact point and evaluate the suitableness of the cocking loosening point of the user swing. In other words, in the cocking loosening feedback apparatus according to an embodiment of the present disclosure, the evaluation variable generating unit may generate a cocking loosening evaluation variable based on the difference between the impact point and the cocking loosening point and the difference between the impact point and the backswing top point.

For example, assuming that on the time axis, the backswing top point and the impact point are respectively $t_b$ and $t_i$ and the cocking loosening point is $t_c$, the cocking loosening may be evaluated according to Equation 2 below.

$$K = \frac{t_i - t_c}{t_i - t_b} \quad \langle \text{Equation 2} \rangle$$

In Equation 2, K is a cocking loosening evaluation variable, which has a value between 0 and 1 and represents as better cocking loosening as closer to the predetermined constant value.

In the cocking loosening feedback apparatus 100 according to an embodiment of the present disclosure, the evaluation variable generating unit 208 may receive the cocking loosening evaluation information transmitted from the analyzing unit 206 and generate a cocking loosening evaluation variable in the golf swing corresponding thereto.

The cocking loosening feedback apparatus according to an embodiment of the present disclosure may include the output unit 210 which may output the evaluation result to the user. The output unit 210 may receive the cocking loosening evaluation variable and output a graded feedback and score or the like. The feedback comment and score provided to the user may be generated according to the cocking loosening evaluation variable based on the information collected from a golf swing specialist group and stored in the apparatus (the data storage unit, 204). For example, in the cocking loosening feedback apparatus according to an embodiment of the present disclosure, the evaluation variable generating unit may generate the feedback and score shown in FIG. 6 if the feedback is generated based on the cocking loosening evaluation variable K illustrated in the cocking evaluation process.

In the cocking loosening feedback apparatus according to an embodiment of the present disclosure, the output unit 210 may provide a feedback to the user through multimedia data such as audio and video data. In other words, the user may recognize the feedback information, namely the feedback comment and score output from the device described above, through a display device or a sound device (a speaker) under the environment of a graphic-based interface or voice-based interface. In addition, according to an embodiment of the present disclosure, the output unit may provide the feedback information to the user based on the relation table about the cocking loosening evaluation variable stored in the data storage unit, and feedback information may be a feedback comment or score.

The cocking loosening feedback method according to an embodiment of the present disclosure may include sensing three-dimensional direction information of a golf club and three-dimensional direction information of the arm in a golf swinging motion of a user (S701), collecting, synchronizing and storing the sensed three-dimensional direction information (S702), analyzing an angle between the three-dimensional direction information of the golf club and the three-dimensional direction information of the arm with respect to time to extract a backswing top point, a cocking loosening point and an impact point based on the stored data information (S703, S704, S705), generating a cocking loosening evaluation variable of the user based on the difference between the cocking loosening point and the impact point and the difference between the backswing top point and the impact point (S706), and providing feedback information to the user based on the cocking loosening evaluation variable (S707). The feedback information may be a feedback comment or score, or any means which allows a user to recognize his cocking loosening point, without being limited thereto.

In the cocking loosening feedback method according to an embodiment of the present disclosure, the analyzing an angle between both three-dimensional direction information with respect to time to extract a backswing top point, a cocking loosening point and an impact point based on the stored data information (S703, S704, S705) may include calculating the change of a cocking angle in the three-dimensional direction information and a relative angle change of the golf club based on the location of the golf club at an address posture (S704), and extracting the backswing top point, the cocking loosening point and the impact point based on the calculation result (S705).

In addition, in the generating a cocking loosening evaluation variable according to an embodiment of the present disclosure, the cocking loosening evaluation variable may be generated by calculating a K value by using Equation 2 above, and in the providing a feedback comment and score, the feedback information may be provided to the user through a display device or a sound device (a speaker) based on the K value and the table shown in FIG. 6.

The above method may be implemented as various computer-executable programs and recorded in a computer-readable medium. The computer-readable medium may include program commands, data files, data structures or the like, solely or in combination.

While the exemplary embodiments have been shown and described, it will be understood by those skilled in the art that various changes in form and details may be made thereto without departing from the spirit and scope of the present disclosure as defined by the appended claims. In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A cocking loosening feedback apparatus, comprising:
   a sensing unit configured to sense three-dimensional direction information of a golf club and of an arm of a user during a golf club swinging motion by the user, the golf club swinging motion comprising a user swing;
   an analyzing unit configured to analyze an angle between the golf club and the arm based on the three-dimensional direction information with respect to time to extract a backswing top time, a cocking loosening time and an impact time;
   an evaluation variable generating unit configured to generate a cocking loosening evaluation variable of the user based on the difference between the cocking loosening time and the impact time and the difference between the backswing top time and the impact time and a closeness of the cocking loosening time existing between the backswing top time and the impact time to the impact time; and
   an output unit comprising a display device or a sound device and configured to provide feedback information to the user based on the cocking loosening evaluation variable,
   wherein the cocking loosening evaluation variable represents a suitableness of the cocking loosening time of the user swing.

2. The cocking loosening feedback apparatus according to claim 1, wherein the analyzing unit comprises:
   a calculating unit configured to calculate a change of a cocking angle in the three-dimensional direction information and a relative angle change of the golf club based on a location of the golf club at an address posture; and
   a time extracting unit configured to extract the backswing top time, the cocking loosening time and the impact time based on the calculated change of the cocking angle.

3. The cocking loosening feedback apparatus according to claim claim 1, wherein the sensing unit comprises an Inertial Measurement Unit (IMU) sensor or a vision sensor, which is attached to the body of the user.

4. The cocking loosening feedback apparatus according to claim 1, wherein the evaluation variable generating unit defines the cocking loosening evaluation variable according to the following equation:

$$K = \frac{t_i - t_c}{t_i - t_b}$$

where K represents the cocking loosening evaluation variable, $t_b$ represents the backswing top time, $t_i$ represents the impact time, and $t_c$ represents the cocking loosening time.

5. The cocking loosening feedback apparatus according to claim 1, further comprising a data storage unit configured to store the sensed three-dimensional direction information,
   wherein the analyzing unit is configured to analyze the angle between the golf club and the arm based on the three-dimensional direction information stored in the data storage unit.

6. The cocking loosening feedback apparatus according to claim 1, wherein the output unit is configured to provide the feedback information to the user by using the display device having a graphic-based interface or the sound device having a voice-based interface.

7. A cocking loosening feedback method, comprising:
   sensing, by a sensing unit, three-dimensional direction information of a golf club and of an arm of a user during a golf club swinging motion by the user, the golf club swinging motion comprising a user swing;
   analyzing, by an analyzing unit, an angle between the golf club and the arm based on the three-dimensional direction information with respect to time to extract a backswing top time, a cocking loosening time and an impact time;
   generating, by a generating unit, a cocking loosening evaluation variable of the user based on the difference between the cocking loosening time and the impact time and the difference between the backswing top time and the impact time and a closeness of the cocking loosening time existing between the backswing top time and the impact time to the impact time; and
   providing, by an output unit, feedback information to the user based on the cocking loosening evaluation variable via the output unit comprising a display device or a sound device,
   wherein the cocking loosening evaluation variable represents a suitableness of the cocking loosening time of the user swing.

8. The cocking loosening feedback method according to claim 7, wherein said analyzing includes:
   calculating a change of a cocking angle in the three-dimensional direction information and a relative angle change of the golf club based on a location of the golf club at an address posture
   extracting the backswing top time, the cocking loosening time and the impact time based on the calculated angle change.

9. The cocking loosening feedback method according to claim 8, wherein said calculating of a cocking angle in the three-dimensional direction information is defined according to the following equation:

$$x_{arm} \cdot x_{club} = \|x_{arm}\| \|x_{club}\| \cos(\theta), 0 \leq \theta \leq \pi$$

where $\theta$ represents the cocking angle, $x_{arm}$ represents a three-dimensional direction vector of the arm, and $x_{club}$ represents a three-dimensional direction vector of the golf club.

10. The cocking loosening feedback method according to claim 7, wherein said providing of feedback information provides the feedback information to the user based on a relation table for a feedback comment and a score, which corresponds to a previously stored cocking loosening evaluation variable.

11. The cocking loosening feedback method according to claim 8, wherein, in said extracting of the backswing top time, the cocking loosening time and the impact time, the backswing top time is a time where a relative turning angle of the golf club has an angular speed of 0 based on an address time, the impact time is a time where the angular speed of the relative turning angle of the golf club changes from a negative value to a positive value based on the address time, and the cocking loosening time is a time where the cocking angle has a minimum value after the backswing top time.

12. The cocking loosening feedback method according to claim 7, wherein said generating of a cocking loosening evaluation variable defines the cocking loosening evaluation variable according to the following equation:

$$K = \frac{t_i - t_c}{t_i - t_b}$$

where K represents the cocking loosening evaluation variable, $t_b$ represents the backswing top time, $t_i$ represents the impact time, and $t_c$ represents the cocking loosening time.

13. The cocking loosening feedback method according to claim 7, further comprising:
collecting, synchronizing and storing the sensed three-dimensional direction information wherein, said analyzing of the angle is performed based on the stored three-dimensional direction information.

14. The cocking loosening feedback method according to claim 7, wherein said providing of feedback information to the user provides the feedback information to the user by using a display device or a sound device having a graphic-based interface or a voice-based interface.

* * * * *